(12) United States Patent
Stopek et al.

(10) Patent No.: US 8,292,068 B2
(45) Date of Patent: *Oct. 23, 2012

(54) MEDICAL DEVICE PACKAGE

(75) Inventors: Joshua B. Stopek, Yalesville, CT (US); David Kirsch, Madison, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/292,129

(22) Filed: Nov. 9, 2011

(65) Prior Publication Data
US 2012/0048751 A1 Mar. 1, 2012

Related U.S. Application Data

(63) Continuation of application No. 12/528,561, filed as application No. PCT/US2008/002458 on Feb. 26, 2008, now Pat. No. 8,069,980.

(60) Provisional application No. 60/904,927, filed on Mar. 5, 2007.

(51) Int. Cl.
*A61B 17/06* (2006.01)
*B65D 83/10* (2006.01)

(52) U.S. Cl. ..... 206/63.3; 206/363; 206/438; 220/254.6

(58) Field of Classification Search .......... 206/363–366, 206/368, 369, 63.3, 63.5, 438; 53/467, 468, 53/473, 476, 396; 220/254.1–254.9, 255, 256.1, 259.1, 259.2, 200, 810
See application file for complete search history.

(56) References Cited

U.S. PATENT DOCUMENTS

| 562,173 | A | | 6/1896 | Daniels |
| 4,896,767 | A | | 1/1990 | Pinheiro |
| 5,024,322 | A | | 6/1991 | Holzwarth |
| 5,366,081 | A | | 11/1994 | Kaplan et al. |
| 5,681,740 | A | * | 10/1997 | Messier et al. ............. 206/438 |
| 6,234,327 | B1 | * | 5/2001 | Reed ............................ 206/63.3 |
| 6,422,411 | B1 | | 7/2002 | Gray |
| 6,460,718 | B1 | | 10/2002 | Vogel |
| 6,648,133 | B1 | | 11/2003 | Blaschke et al. |
| 2006/0027467 | A1 | | 2/2006 | Ferguson |

FOREIGN PATENT DOCUMENTS
WO    WO 99/37233 A1    7/1999

OTHER PUBLICATIONS
International Search Report for PCT/US2008/002458 date of completion is Jun. 10, 2008 (2 pages).

* cited by examiner

*Primary Examiner* — Luan K Bui

(57) ABSTRACT

The present disclosure provides a package for a medical device containing a cavity for receiving the medical device, a first closure having a sealed portal therein and a second closure adjacent the first closure.

16 Claims, 3 Drawing Sheets

MEDICAL DEVICE PACKAGE

CROSS-REFERENCE TO RELATED APPLICATIONS

This application is a continuation of U.S. application Ser. No. 12/528,561 filed Aug. 25, 2009, now U.S. Pat. No. 8,069,980, which is a National Stage Application of PCT/US2008/002458 under 35 USC §371(a), filed Feb. 26, 2008, which claims priority to U.S. Provisional Patent Application Ser. No. 60/904,927 filed Mar. 5, 2007, the disclosures of each of the above-identified applications are hereby incorporated by reference in their entirety.

BACKGROUND

1. Technical Field

The present disclosure relates generally to a package for medical devices, and more particularly, to a package including a first cavity for receiving a medical device, a first closure for sealing the medical device within the first cavity, the first closure including a sealed portal defined therein and a second closure positioned adjacent the first closure, the second closure surrounding the portal.

2. Background of Related Art

Combination medical devices, i.e., medical devices coated with drugs or other bioactive agents, have become more prevalent commercially in recent years. There are many of these combination medical devices known to those skilled in the art. Many of these devices require specialized coatings to facilitate both bioactive agent elution and, more importantly, maintain or enhance the core functionality of the medical device. For example, a suture containing an antimicrobial coating must be able to facilitate the elution of the antimicrobial agent in the coating and also maintain a certain tensile strength, handling ability, knot-tying ability, and degradation rate to ensure the coated suture remains functional as a wound closure device.

Further, with the selection of a new coating, drug or any combination of medical devices comes the challenge of marrying the selected agents with a coating or medical device that can accommodate both technical requirements described above, as well as the manufacturing, sterilizing, and transporting processes involved in producing such products. This often requires the design of new coating polymers, which are specialized to be compatible with a specific agent, as well as new coating, manufacturing, sterilizing and transporting processes. In addition, designing these new coatings and processes creates the added pressures of possibly impacting the shelf-life of the device as well as the end-use of the combination medical device in a negative manner.

Also, medical professionals are limited to using the combination medical device in the dosage and strength produced, without flexibility to alter the product as needed for their respective patients.

Therefore, the present disclosure describes a package for a medical device aimed at simplifying the design and application of combination medical device coatings to provide the following benefits: the ability to choose any bioactive or non-bioactive agent necessary for the individual patient without having to change existing products or manufacturing process; sensitive agents can be delivered without compromising standard shelf or transport conditions; the ability to later combine a specific medical device with agents that were unable to tolerate the required sterilization process for that specific device, under sterile conditions; the medical professional has greater control over product selection; and longer shelf-life of products due to more stable format.

SUMMARY

A package for a medical device in accordance with the present disclosure includes a cavity configured and dimensioned to receive a medical device, a first closure for sealing the medical device within the cavity, the first closure including a sealed portal therein for accessing the medical device and a second closure positioned adjacent the first closure and surrounding the sealed portal.

BRIEF DESCRIPTION OF THE DRAWINGS

Various embodiments are described herein with reference to the drawings wherein.

DETAILED DESCRIPTION

Figure 1:
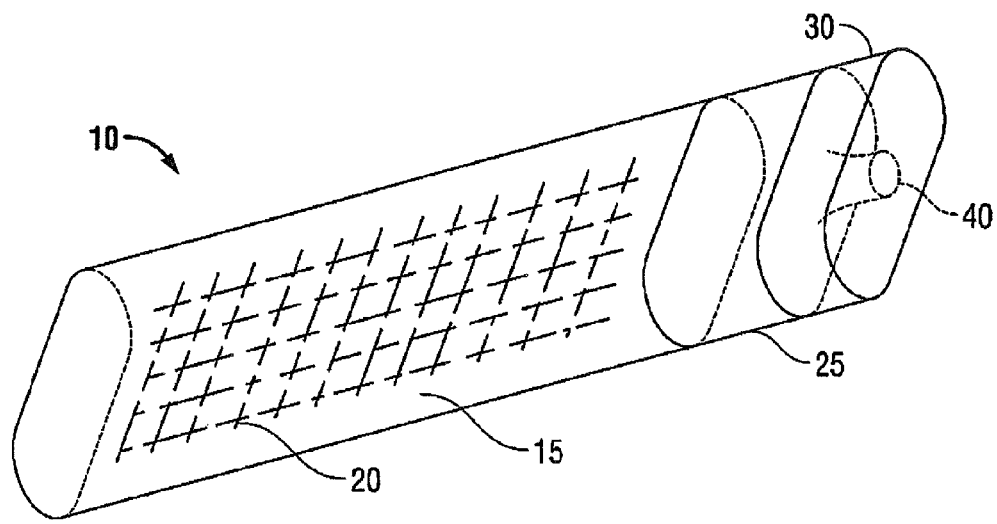
FIG. 1 is a perspective view of a package for a medical device in a closed position.

The present disclosure describes packages for one or more medical device(s) which include a cavity which is configured and dimensioned to receive a medical device. The packages also include a first closure and a second closure. The first closure includes a sealed portal and is designed to seal the medical device within the cavity. The second closure is positioned adjacent the first closure with the ability to surround the sealed portal. The sealed portal is defined within the first closure and allows for the passage of an agent between the outside of the package and the inside of the cavity.

It is envisioned that the first closure which includes a sealed portal defined therein and the second closure which is positioned adjacent the first closure may be positioned together along any side, edge or corner of the package. The first closure being dimensioned appropriately to seal the cavity which receives the medical device while including room to have a sealed portal defined therein. The second closure being dimensioned appropriately to surround the sealed portal defined within the first closure. In embodiments, the first and second closure may be made of the same size and dimension. In other embodiments, the first and second closures may be made of different size and dimension.

The sealed portal which is defined within the first closure is designed to permit the passage of at least one agent between the outside of the package and the medical device positioned within the cavity. It is envisioned that the portal may be made of any size, shape or dimension and may also be positioned along any side, edge or corner of the first closure.

In embodiments, the portal may be an injectable-hub which is designed to remain sealed by self-sealing action to ensure no fluid medium can escape and also so no pathogens can breach the package. The injectable-hub would require a delivery device to include some sort of sharpened edge to penetrate the hub such as a needle or beveled edge of intravenous tubing systems. The portal can be composed of a traditional rubber or thermoplastic material known to be used in sealing sterile vials, intravenous bags, catheters, drug ampules or blood bags. Alternatively, the portal may be composed of hydrophobic, hydrophilic or a combination of hydrophobic and hydrophilic materials.

In embodiments, the portal may be a hub designed in such a way that only a particular syringe can mate with the portal thereby creating a lock and key type of hub to promote only specific use of the portal. This type of portal provides more safety to the user of portal because the portal does not necessarily require the use of a needle. In addition, the lock and key type of hub may be used by patients and medical staff for only certain medications and dosages of those medications, thereby reducing the likelihood of administering the wrong agent or the wrong dosage of the intended agent.

The sealed portal may be accessed to allow the passage of at least one agent between the outside of the package and the inside of the cavity. The agent may be passed through the sealed portal as a solid, liquid, semi-solid, gas, or any combination thereof. The at least one agent may be selected from any bioactive and/or non-bioactive agent suitable for combination with the medical device. Suitable agents include, but are not limited to, drugs, such as antiseptics, anesthetics, muscle relaxants, antihistamines, decongestants, antimicrobial agents, anti-viral agents, anti-fungal agents, antimalarials, amebicides, antituberculosal agents, antiretroviral agents, leprostatics, antiprotazoals, antihelmitics, antibacterial agents, steroids, hematopoietic agents, antiplatelet agents, anticoagulants, coagulants, thrombolytic agents, hemorrheologic agents, hemostatics, plasma expanders, hormones, sex hormones, uterine-active agents, bisphosphonates, antidiabetic agents, glucose-elevating agents, growth hormones, thyroid hormones, inotropic agents, antiarrhythmic agents, calcium channel blockers, vasodilators, sympatholytics, antihyperlipidemic agents, vasopressors, angiotensin antagonists, sclerosing agents, anti-impotence agents, urinary alkanizers, urinary acidifiers, anticholinergics, diuretics, bronchodilators, surfactants, antidepressants, antipsychotics, antianxiety agents, sedatives, hypnotics, barbiturates, antiemetic agents, analgesics, stimulants, anticonvulsants, antiparkinson agents, proton pump inhibitors, $H_2$-antagonists, antispasmodics, laxatives, antidiarrheals, antiflatulents, digestive enzymes, gallstone solubilizing agents, antihypertensive agents, cholesterol-lowering agents, radiopaque agents, immune globulins, monoclonal antibodies, antibodies, antitoxins, antivenins, immunologic agents, anti-inflammatory agents, antineoplastic agents, alkylating agents, antimetabolites, antimitotic agents, radiopharmaceuticals, vitamins, herbs, trace elements, amino acids, enzymes, chelating agents, immunomodulatory agents and immunosuppressive agents; coating materials such as lubricants, and non-bioabsorbable substances such as silicone, beeswax, or polytetrafluoroethylene, as well as absorbable substances such as collagen, chitosan, chitin, carboxymethylcellulose, and homopolymers and/or copolymers of polyalkylene glycols, and higher fatty acids or salts or esters thereof, glycolic acid, a glycolide, lactic acid, a lactide, p-dioxanone, valerolactone and other lactones derived from linear aliphatic hydroxycarboxylic acids, α-hydroxybutyric acid, ethylene carbonate, ethylene oxide, propylene oxide, propylene carbonate, malic acid ester lactones, succinic acid, adipic acid and other linear aliphatic dicarboxylic acids, and linear aliphatic diols such as butanediol and hexanediol; wound healing agents; adhesives; sealants; blood products; blood components; preservatives; colorants; dyes; ultraviolet absorbers; ultraviolet stabilizers; photochromic agents; anti-adhesives; proteins; polysaccharides; peptides; genetic material; viral vectors; nucleic acids; nucleotides; plasmids; lymphokines; radioactive agents; metals; alloys; salts; growth factors; growth factor antagonists; cells; hydrophobic agents; hydrophilic agents; immunological agents; anti-colonization agents; diagnostic agents; imaging agents; cross-linking agents; and diluents, such as water, saline, dextrose. Of course any combination of these agents may also be passed to the medical device contained in the package.

The packages as described herein may be made from a variety of materials or combination of materials. Some suitable materials for forming the packages described herein include, but are not limited to, polymeric materials, thermoplastic materials, ceramic materials, metallic materials and combinations thereof. The materials may be transparent, semi-transparent or opaque. Although any natural or synthetic polymeric material may be used to form the packages, some non-limiting examples include polymers, copolymers, homopolymers, block copolymers, and random copolymers including materials such as polyethylene, polypropylene, polycarbonates, polyesters, polycaprolactone, polyethylene terphthalate, and polysiloxanes.

The size and shape of the package is selected to provide a cavity appropriate to receive a particular medical device or devices. For example, packages for a vascular graft or tissue-based implant are generally cylindrical, while packages for a mesh, suture and the like are generally rectangular. Since medical devices vary in size and shape, it is envisioned that the size and shape of the packages described herein may vary accordingly to accommodate such devices. For example, the packages described herein may be generally rectangular, circular, octagonal, cylindrical, pentagonal, hexagonal, and the like.

In embodiments, the medical device may be withdrawn from the original container in which it was stored or shipped and placed within the cavity of the package. In embodiments, the medical device may remain positioned within the original container in which it was stored or shipped and the entire container including the medical device may be received within the cavity of the packages described herein.

The packages are configured and dimensioned to receive any medical device. Any medical device may be received within the package, including implantable, transplantable or prosthetic materials which are designed to remain in the body for at least some time.

Appropriate medical devices can be made from natural material, synthetic material or a combination of natural and synthetic material. Examples of natural materials include, for example, intact tissues as well as decellularized tissue. These tissues are often derived from a particular animal species such as human, bovine, porcine, shark and the like, and may be obtained from, for example, natural heart valves; portions of natural heart valves such as roots, walls and leaflets; pericardial tissues such as pericardial patches; connective tissues; bypass grafts; tendons; ligaments; skin patches; blood vessels; cartilage; dura matter; skin; bone; umbilical tissues; GI tract tissues; and the like. These natural tissues generally include collagen-containing material.

The devices may also be formed from tissue equivalents such as a tissue-engineered material involving a cell-repopulated matrix, which can be formed from polymers, biopolymers or from a decellularized natural tissue. Biopolymers can be naturally occurring or produced in vitro by, for example, fermentation and the like. Purified biopolymers can be appropriately formed into a substrate by techniques such as weaving, knitting, casting, molding, extrusion, cellular alignment and magnetic alignment.

Synthetic materials that can be used to form the medical devices described herein include a variety of biocompatible materials such as metals, polymers, ceramics and combinations thereof. Appropriate polymers include, for example, hydrogels, bioabsorbable materials and non-bioabsorbable materials.

Suitable non-limiting examples of medical devices which may be received within the packages described herein, include: sutures, staples, clips, pledgets, buttresses, suture anchors, cables, wires, pacemakers, stents, catheters, inflatable devices, adhesives, sealants, meshes, sternum closures, pins, screws, tacks, rods, plates, adhesion barriers, bioelectronic devices, dental implants, surgical tools and combinations thereof.

Referring now to FIGS. 1-4, package 10 as described herein includes cavity 15 which is configured and dimensioned to receive medical device 20, first closure 25 for sealing medical device 20 within cavity 15, first closure 25 having sealed portal 40 defined therein for accessing medical device 20 and second closure 30 which is positioned adjacent first closure 25 and surrounds sealed portal 40.

In FIG. 1, package 10 is shown in the closed or sealed position. In the closed position, first closure 25 prevents cavity 15 and any contents contained in cavity 15 including medical device 20 from being accessed from outside package 10 except for passage through sealed portal 40. Second closure 30 is adjacent first closure 25 and surrounds sealed portal 40. In the closed position, second closure 30 prevents access to sealed portal 40 thereby preventing the passage of a bioactive agent through sealed portal 40 and between the outside of package 10 and cavity 15.

Figure 2:
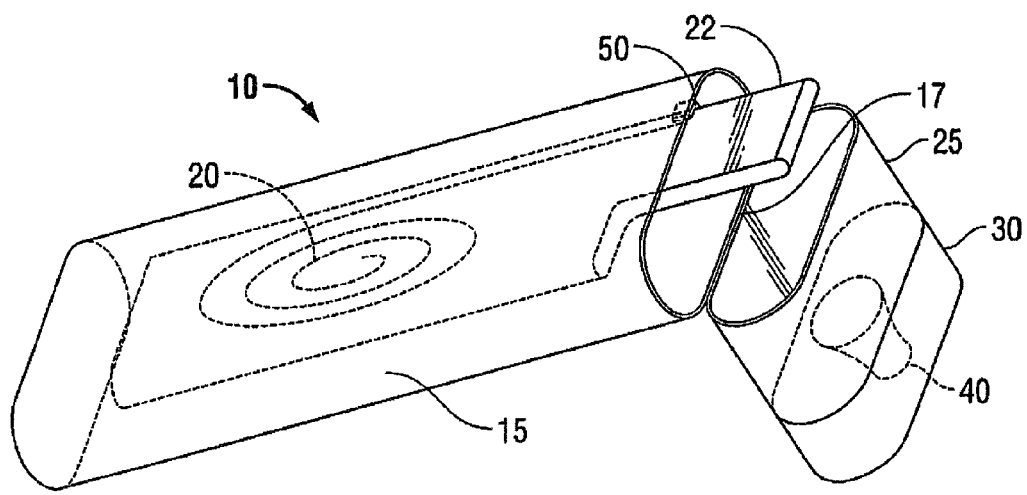
FIG. 2 is a perspective view of a package for a medical device in an open position.

Turning to FIG. 2, package 10 is shown in a first open position wherein first closure 25 is positioned away from cavity 15 thereby allowing direct access into cavity 15 of package 10. In the first open position, a container 22 for storing a medical device 20 may be positioned within or withdrawn from cavity 15. In embodiments, container 22 may be a suture retainer and medical device 20 may be a suture. As shown, second closure 30 may remain surrounding sealed portal 40 and adjacent first closure 25 while package 10 and first closure 25 are positioned in an open position. In embodiments, second closure 30 may also be positioned away from sealed portal 40 to allow access to sealed portal 40 while package 10 and first closure 25 are in the open position (not shown).

First closure 25 may be attached to cavity 15 using any mechanical means suitable for allowing first closure 25 to move from the open position to the closed position as described herein. In embodiments, first closure 25 and cavity 15 may be formed from separate materials as a structure which is not monolithic. The separate materials may be attached to each other using a connecting member. Suitable connecting members include known devices which attach at least a portion of first closure 25 to at least a portion of cavity 15 and allow first closure 25 to pivot about leading edge 17 of cavity 15 to seal medical device 20 with cavity 15. A particularly useful connecting member includes a hinge or hinge-like device.

In embodiments, first closure 25 and cavity 15 are formed as a monolithic structure wherein at least a portion of first closure 25 is directly attached to a portion of cavity 15. The monolithic structure includes a naturally pivotable portion which is positioned along leading edge 17 of cavity 15 which connects first closure 25 to cavity 15 and allows first closure 25 to pivot and seal medical device 20 within cavity 15.

Also in FIG. 2, package 10 is shown receiving medical device 20 including the container 22 which medical device 20 is stored, shipped or manufactured in. In embodiments, container 22 may include a port which is capable of connecting to sealed portal 40 when cavity 15 is closed by first closure 20 (See FIG. 3)

In addition, FIG. 2 shows package 10 further including at least one guide member 50. Guide member 50 is positioned within cavity 15 to assist with the loading of medical device 20 into cavity 15 of package 10. In addition guide member 50 may be utilized to position medical device 20 within cavity 15 at a certain angle, height, depth, etc. Guide member 50 may also be used to prevent medical device 20 from moving around within cavity 15. As shown, guide member 50 is a slot which extends a predetermined length inside cavity 15 and which is dimensioned to receive the edge of medical device 20 thereby locking medical device into position within cavity 15. Suitable guide members include those devices which assist with properly positioning the medical device within cavity 15 and include for example, tabs, tracks, hooks, footings and the like.

Figure 3:
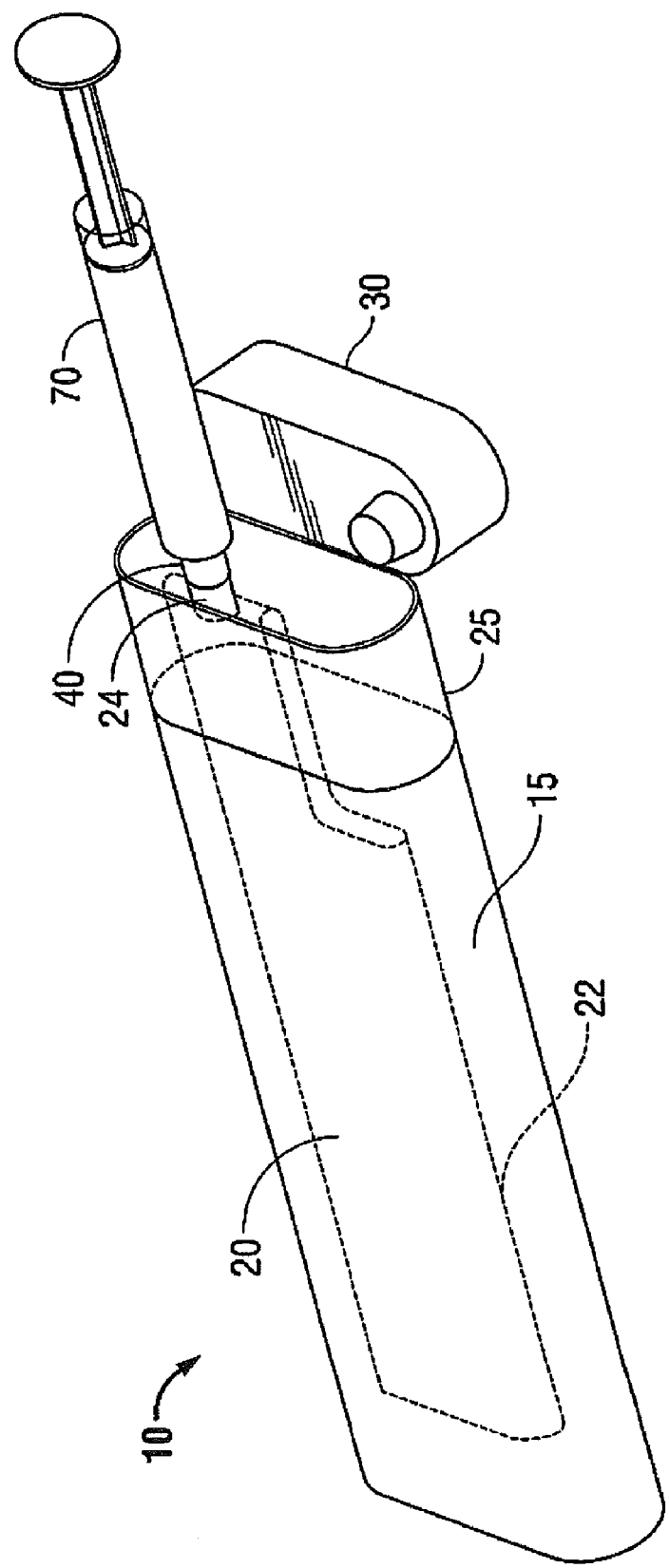
FIG. 3 is a perspective view of a package for a medical device having a delivery device attached to the sealed portal for passing an agent between the outside of the package and the inside of the cavity.

Turning now to FIG. 3, package 10 is shown with medical device 20 sealed within cavity 15 by first closure 25. Second closure 30 is pivoted away from sealed portal 40 thereby allowing delivery device 70 access to sealed portal 40. Medical device 20 is stored in container 22 which includes port 24. Port 24 is positioned on container 22 to engage sealed portal 40 when cavity 15 is sealed by first closure 25. Delivery device 70 is shown accessing sealed portal 40 and in position to permit the passage of an agent between the outside of package 10 and the inside of cavity 15. In embodiments, delivery device 70 may include any device capable of engaging or accessing sealed portal 40 and delivering the agent through sealed portal 40. Suitable non-limiting examples include, needles, syringes, infusion pumps, and IV delivery systems.

Figure 4:
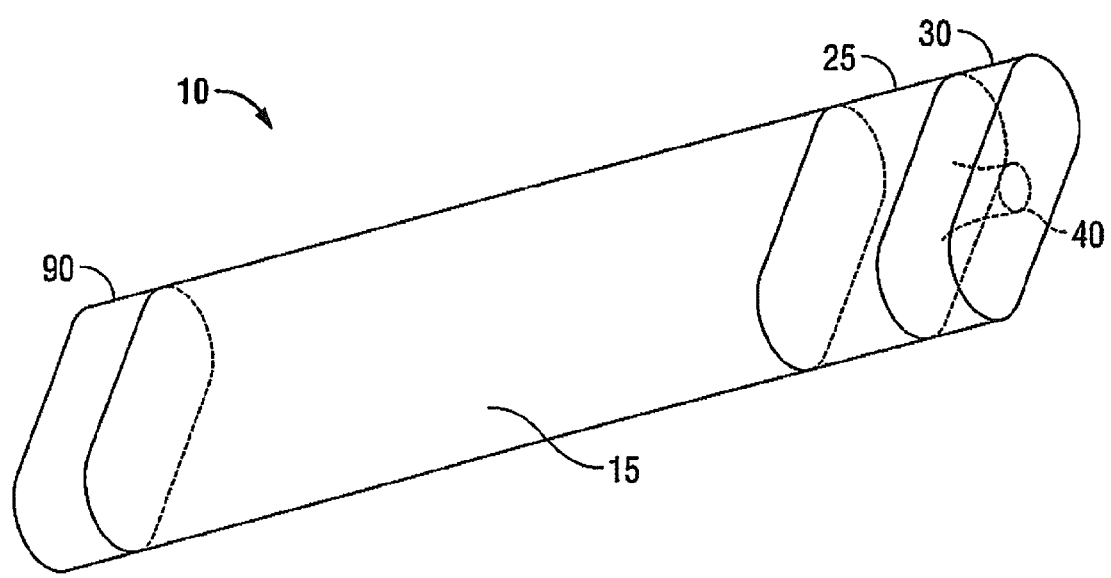
FIG. 4 is a perspective view of a package for a medical device including a third closure.

In embodiments, package 10 may further include third closure 90 as depicted in FIG. 4. Third closure 90 is positioned on the distal end of package 10. As defined herein, the proximal end of package 10 is meant to include the end nearest second closure while the distal end is meant to include the end of package 10 which is farthest from second closure. Third closure 90 is designed to allow medical device 20 from being withdrawn from or received into cavity 15 of package 10.

It is well understood that various modifications may be made to the embodiments disclosed herein. Therefore, the above description should not be construed as limiting, but merely as exemplifications of particularly useful embodiments. Those skilled in the art will envision other modifications within the scope and spirit of the claims appended hereto.

We claim:

1. A package for a medical device, the package comprising:
 a medical device;
 a package housing defining a cavity configured and dimensioned to receive the medical device;
 a first closure positioned at a proximal end of the package housing and movable from an open position to a closed position for sealing the medical device within the cavity, the first closure having a self-sealing injectable hub therein which maintains sterility of the package when accessing the medical device, and,
 a second closure positioned at a distal end of the package housing opposite the proximal end of the package housing.

2. The package of claim 1 wherein the medical device is selected from the group consisting of sutures, staples, clips, pledgets, buttresses, suture anchors, cables, wires, pacemakers, stents, catheters, inflatable devices, adhesives, sealants, meshes, sternum closures, pins, screws, tacks, rods, plates, adhesion barriers, bioelectronic devices, dental implants, surgical tools and combinations thereof.

3. The package of claim 1 wherein the medical device is a suture.

4. The package of claim 1 further comprising at least one agent selected from the group consisting of drugs, coating materials, diluents, wound healing agents, adhesives, sealants, blood products, blood components, preservatives, colorants, dyes, ultraviolet absorbers, ultraviolet stabilizers, photochromic agents, anti-adhesive agents, proteins, polysaccharides, peptides, genetic material, viral vectors, nucleic acids, nucleotides, plasmids, lymphokines, radioactive agents, cross-linking agents, metals, alloys, salts, growth factors, growth factor antagonists, cells, immunological agents, anti-colonization agents, diagnostic agents, imaging agents, and combinations thereof.

5. The package of claim 4 wherein the at least one agent is a drug.

6. The package of claim 5 wherein the drug is selected from the group consisting of antiseptics, anesthetics, muscle relaxants, antihistamines, decongestants, antimicrobial agents, anti-viral agents, anti-fungal agents, antimalarials, amebicides, antituberculosal agents, antiretroviral agents, leprostatics, antiprotazoals, antihelmitics, antibacterial agents, steroids, hematopoietic agents, antiplatelet agents, anticoagulants, coagulants, thrombolytic agents, hemorrheologic agents, hemostatics, plasma expanders, hormones, sex hormones, uterine-active agents, bisphosphonates, antidiabetic agents, glucose-elevating agents, growth hormones, thyroid hormones, inotropic agents, antiarrhythmic agents, calcium channel blockers, vasodilators, sympatholytics, antihyperlipidemic agents, vasopressors, angiotensin antagonists, sclerosing agents, anti-impotence agents, urinary alkanizers, urinary acidifiers, anticholinergics, diuretics, bronchodilators, surfactants, antidepressants, antipsychotics, antianxiety agents, sedatives, hypnotics, barbiturates, antiemetic agents, analgesics, stimulants, anticonvulsants, antiparkinson agents, proton pump inhibitors, H2-antagonists, antispasmodics, laxatives, antidiarrheals, antiflatulents, digestive enzymes, gallstone solubilizing agents, antihypertensive agents, cholesterol-lowering agents, radiopaque agents, immune globulins, monoclonal antibodies, antibodies, antitoxins, antivenins, immunologic agents, anti-inflammatory agents, antineoplastic agents, alkylating agents, antimetabolites, antimitotic agents, radiopharmaceuticals, vitamins, herbs, trace elements, amino acids, enzymes, chelating agents, immunomodulatory agents, immunosuppressive agents and combinations thereof.

7. The package of claim 4 wherein the at least one agent is a diluent selected from the group consisting of water, saline, dextrose and combinations thereof.

8. The package of claim 1 wherein the package is a monolithic structure.

9. The package of claim 1 further comprising at least one guide member positioned within the cavity.

10. A method of packaging a medical device comprising: providing a medical device; and placing the medical device in the package of claim 1.

11. A packaged medical device comprising:
a surgical mesh;
a cavity configured and dimensioned to receive the surgical mesh;
a first closure movable from an open position to a closed position for sealing the surgical mesh within the cavity, the first closure having a self-sealing injectable hub therein which maintains sterility of the package when accessing the surgical mesh and the first closure positioned at a proximal end of the cavity, and a second closure positioned at a distal end of the cavity opposite the proximal end of the cavity.

12. The package of claim 11 further comprising at least one guide member positioned within the cavity.

13. The package of claim 11 further comprising at least one agent selected from the group consisting of drugs, coating materials, diluents, wound healing agents, adhesives, sealants, blood products, blood components, preservatives, colorants, dyes, ultraviolet absorbers, ultraviolet stabilizers, photochromic agents, anti-adhesive agents, proteins, polysaccharides, peptides, genetic material, viral vectors, nucleic acids, nucleotides, plasmids, lymphokines, radioactive agents, cross-linking agents, metals, alloys, salts, growth factors, growth factor antagonists, cells, immunological agents, anti-colonization agents, diagnostic agents, imaging agents, and combinations thereof.

14. The package of claim 13 wherein the at least one agent is a drug selected from the group consisting of antiseptics, anesthetics, muscle relaxants, antihistamines, decongestants, antimicrobial agents, anti-viral agents, anti-fungal agents, antimalarials, amebicides, antituberculosal agents, antiretroviral agents, leprostatics, antiprotazoals, antihelmitics, antibacterial agents, steroids, hematopoietic agents, antiplatelet agents, anticoagulants, coagulants, thrombolytic agents, hemorrheologic agents, hemostatics, plasma expanders, hormones, sex hormones, uterine-active agents, bisphosphonates, antidiabetic agents, glucose-elevating agents, growth hormones, thyroid hormones, inotropic agents, antiarrhythmic agents, calcium channel blockers, vasodilators, sympatholytics, antihyperlipidemic agents, vasopressors, angiotensin antagonists, sclerosing agents, anti-impotence agents, urinary alkanizers, urinary acidifiers, anticholinergics, diuretics, bronchodilators, surfactants, antidepressants, antipsychotics, antianxiety agents, sedatives, hypnotics, barbiturates, antiemetic agents, analgesics, stimulants, anticonvulsants, antiparkinson agents, proton pump inhibitors, H2-antagonists, antispasmodics, laxatives, antidiarrheals, antiflatulents, digestive enzymes, gallstone solubilizing agents, antihypertensive agents, cholesterol-lowering agents, radiopaque agents, immune globulins, monoclonal antibodies, antibodies, antitoxins, antivenins, immunologic agents, anti-inflammatory agents, antineoplastic agents, alkylating agents, antimetabolites, antimitotic agents, radiopharmaceuticals, vitamins, herbs, trace elements, amino acids, enzymes, chelating agents, immunomodulatory agents, immunosuppressive agents and combinations thereof.

15. The package of claim 13 wherein the at least one agent is a diluent selected from the group consisting of water, saline, dextrose and combinations thereof.

16. The package of claim 11 wherein the package is a monolithic structure.

* * * * *